United States Patent [19]
MacLean

[11] Patent Number: 5,259,390
[45] Date of Patent: Nov. 9, 1993

[54] METHOD AND APPARATUS TO MONITOR SLEEP BEHAVIOUR

[75] Inventor: Alistair W. MacLean, Kingston, Canada

[73] Assignee: Queen's University, Kingston, Canada

[21] Appl. No.: 829,203

[22] Filed: Feb. 3, 1992

[51] Int. Cl.⁵ ............................................. A61B 5/00
[52] U.S. Cl. .................................................. 128/739
[58] Field of Search ................... 128/739, 774, 782; 600/26, 27; 340/573, 575

[56] References Cited

U.S. PATENT DOCUMENTS

| | | | |
|---|---|---|---|
| 3,363,242 | 1/1968 | Currey et al. | 128/782 |
| 4,617,525 | 10/1986 | Lloyd | 128/716 |
| 4,836,219 | 6/1989 | Hobson et al. | 128/782 |

FOREIGN PATENT DOCUMENTS

| | | | |
|---|---|---|---|
| 1503745 | 8/1989 | U.S.S.R. | 128/739 |
| 1553055 | 3/1990 | U.S.S.R. | 128/739 |

Primary Examiner—Max Hindenburg
Attorney, Agent, or Firm—Richard J. Hicks

[57] ABSTRACT

A vibrating stimulus-response device and method to monitor sleep behaviour is described. The self-contained portable device can be used in a home environment as a preliminary screen before a more extensive polysomnographic examination.

12 Claims, 2 Drawing Sheets

METHOD AND APPARATUS TO MONITOR SLEEP BEHAVIOUR

FIELD OF INVENTION

This invention relates to a method and apparatus to monitor sleep and wakefulness in a human subject. More particularly this invention relates to a vibratory stimulus-response device to monitor sleep behaviour.

BACKGROUND OF INVENTION

Sleep can be assessed subjectively, behaviourally or physiologically. Of these three approaches, electrophysiological recordings have over the last thirty-five years become the standard approach. This approach-polysomnography-requires that electrodes be attached to the subject, using standard positions, for the continuous monitoring of electroencephalographic (EEG), electroculographic (EOG) and electromyographic (EMG) activity. The resulting record is scored into various sleep stages according to internationally accepted criteria (Rechtschaffen & Kales, 1968. "A manual of standardized terminology, techniques and scoring system for sleep stages of human subjects." Brain Information Service/Brain Research Institute, Los Angeles, Calif.)

While electrophysiological techniques have the advantage of being non-invasive, relatively unobtrusive, and being well tolerated, they have a number of practical disadvantages. Their application usually requires the subject or patient to come to a sleep clinic or laboratory for an overnight stay under the constant supervision of a trained technician, who will spend up to an hour and a half connecting and disconnecting the patient to the polygraph, and several hours monitoring the sleeping patient. Such a study will generate an enormous paper record—of the order of one third of a mile long, which must be scored and evaluated by trained personnel. The mathematical reduction of the data is not trivial. Thus the electrophysiological testing methods are cumbersome, expensive and not readily adaptable to ambulatory or home based monitoring.

In addition, there are a number of substantive issues which bear on the efficacy of the physiological assessment of sleep. While electrophysiological techniques assess certain important aspects of sleep, they ignore others. Specifically, they do not assess behaviour directly. The presence of a particular type of brain activity is not an infallible guarantee that an individual will be able to make a specific response such as identifying a warning signal on a nuclear reactor or navigating a vehicle on a motorway. This issue is also pertinent to the assessment of individuals complaining of sleep disorder. At any given time about one third of the general population over the age of eighteen is likely to complain of having insomnia while a small proportion complain of being excessively sleepy. The number of individuals being referred for sleep-related complaints has increased markedly over the last two decades and continues to increase as do the number of specialist centres devoted to their assessment and treatment. While polysomnography has an important role in this, its application is limited by its availability and by its appropriateness. Even a large sleep disorders centre can only see about twelve patients nightly or about 4000 patients a year while most facilities can only handle 300-1000 patients per year. Also, polysomnography does not address all relevant aspects of a disorder. Many insomnia patients complain of excessive sensitivity to environmental stimulation while many excessively sleepy patients complain of failing to respond adequately to environmental stimulation.

There is, therefore, a considerable need for a simple method and apparatus for sleep monitoring which would measure relevant aspects of behaviour, would be suitable for home use, could be used to provide a preliminary screen to quickly and efficiently identify patients in need of a more intensive evaluation. A wider spectrum of relevant behaviour could be assessed, the costs of the polysomnographic examination may be avoided and the frustration of long patient waiting lists may be reduced.

OBJECT OF INVENTION

Thus, it is one object of the present invention to provide a simple vibratory stimulus response device to monitor sleep and wakefulness in a human subject.

Another object is to provide a method for assessing sleep behaviour in a human subject.

BRIEF STATEMENT OF INVENTION

Thus by one aspect of this invention there is provided an apparatus for monitoring sleep behaviour in a human subject comprising:

a housing; vibratory means and subject response means contained within said housing; timing means to activate said vibratory means at selected time intervals; means to record and store each activation event of said vibratory means, and subject positive and negative response thereto; and means to retrieve and analyze said records.

By another aspect of this invention there is provided a method for assessing sleep behaviour in a human subject, comprising:

(a) subjecting the subject to a vibratory stimulus at selected spaced intervals of time;

(b) recording the time of each said stimulus and the subject's response or lack thereof to each said stimulus;

(c) recovering stored information; and (d) assessing the subject by comparison of said recovered stored information with known standards of sleep behaviour.

DETAILED DESCRIPTION OF PREFERRED EMBODIMENTS

Figure 1:
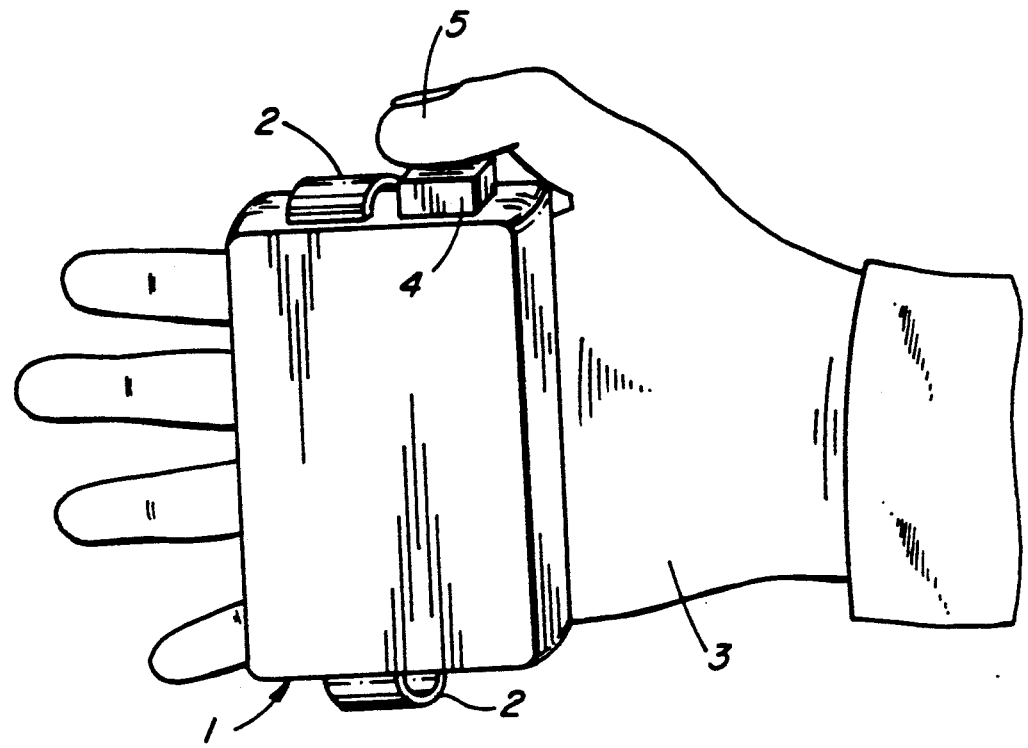
FIG. 1 is a sketch of a hand-held unit incorporating the invention.

As shown in FIG. 1, a preferred embodiment of the invention comprises a self-contained vibrator and data storage unit 1 which is about 4 inches long, 3.5 inches wide, and 0.5 inches thick, which may be hand-held. For convenience, and to prevent loss during sleep, the unit 1 is provided with a strap loop 2 through which the hand 3 is slipped so as to hold the unit firmly in the palm of the hand. A response button 4, such as a spring loaded micro switch, is conveniently located at one end of the unit so that it can be readily activated by the thumb 5. It will, of course, be appreciated that the location and design of the response button is merely a matter of design choice and numerous alternatives will be readily apparent to those skilled in the art.

Figure 2:
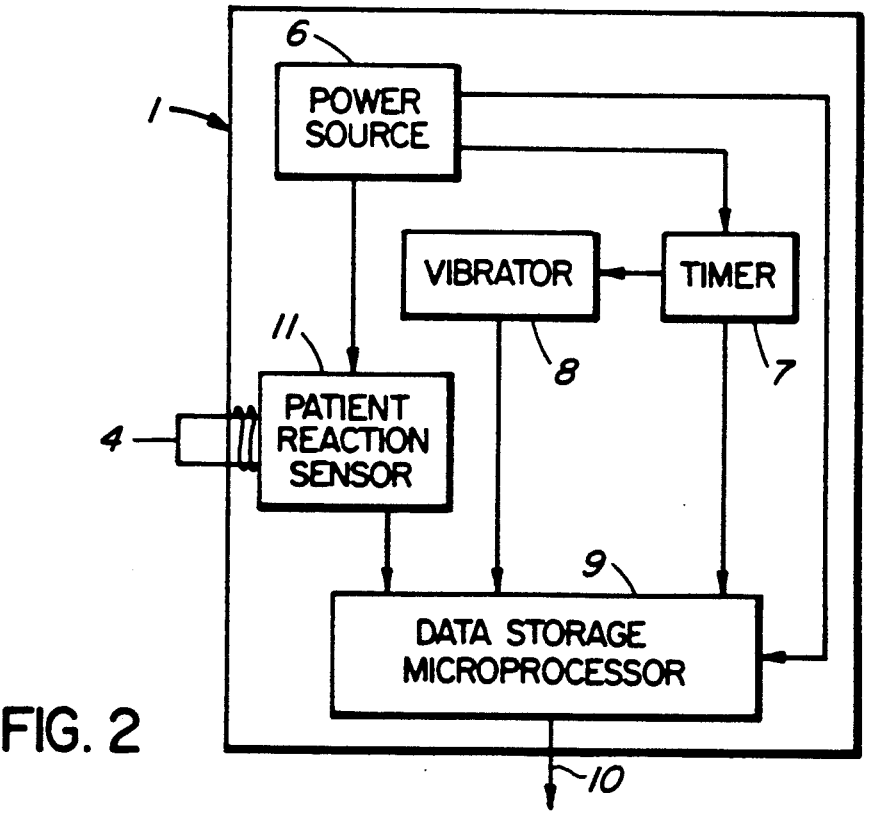
FIG. 2 is a schematic block diagram of one embodiment of the invention.

As shown in FIG. 2, the housing 1 contains a power source for a patient response sensor 11, a timing circuit 7, an electro tactile vibrating unit 8 (such as a Tactile Vibrator, supplied by Audiological Engineering Corp., Summerville, Mass.) and a microprocessor 9, which is provided with a signal output 10 which should be compatible with a computer interface. The power source 6 is conveniently, but not essentially, a conventional long-life dry cell which provides sufficient power to operate the timing circuit, the vibrator and the microprocessor. It will be appreciated that while preferred, it is by no means essential that power source 6 be internal to unit 1. An external power source with appropriate lead in wires is also within the scope of this invention.

The vibrator 8 is preferably an electro tactile vibrator which provides a 20-40 Hz bandwidth at the selected frequency of 160-200 Hz and preferably 180 Hz. The timer may be set to trigger the vibrator on either a random basis or, more usually, on a timed basis of the order of a 0.5 second pulse every 5-10 minutes. The vibrations are of sufficiently low amplitude that they are unlikely to provoke any sleep disturbance in a sleeping patient. The time of each vibratory event whether or not the patient makes a response to that event and the time taken to make that response may be recorded in the microprocessor data storage device. The stored data may be recovered for later analysis using a conventional computer interface.

Experimental Procedures

Twelve healthy, volunteer, young, female subjects who were medication free were recruited to compare the vibratory stimulus unit to standard polysomnographic monitoring during a single night of sleep monitoring. Before going to sleep the subjects had electrodes attached as described above for electrophysiological monitoring: the resulting sleep records were scored according to standard criteria. They then had the vibratory stimulus device 1 described above fitted to their preferred hand. The subjects were instructed to sleep normally and press switch 4 whenever they felt a vibratory stimulus. The stimulus was a 180 Hz vibration administered with a maximum peak-to-peak output of 1150 mV for 0.5 seconds at an average inter-stimulus interval of 7.5 minutes.

A polysomnographic recording classifies sleep in several stages systematized by an international committee (Recht-schaffen & Kales, 1968. "A manual of standardized terminology, techniques and scoring system for sleep stages in human sleep subjects. Brain Information Service/Brain Research Institute, Los Angeles). The major characteristics are summarized in Table 1.

TABLE 1

| \multicolumn{2}{l}{Table of the Major Characteristics of the Stage of Sleep} |  |
|---|---|
| Stage | Major Characteristics |
| Awake | Alpha activity and/or low voltage, mixed frequency EEG. |
| Stage 1 | Relatively low voltage, mixed frequency EEG. Highest voltage is about 50–75 $\mu$V and tends to occur in bursts mostly towards the latter position of the stage. |
| Stage 2 | Defined by the presence of sleep spindles and/or K complexes and the absence of sufficient high |

TABLE 1-continued

| \multicolumn{2}{l}{Table of the Major Characteristics of the Stage of Sleep} |  |
|---|---|
| Stage | Major Characteristics |
|  | voltage, slow activity to define Slow Wave Sleep. |
| Stage 3[b] | A record in which at least 20% of the epoch consists of waves of 2 cps[a] or slower and amplitudes greater than 75 $\mu$V peak-to-peak. |
| Stage 4[b] | An EEG record in which more than 50% of an epoch consists of waves of 2 cps[a] or slower and with amplitudes greater than 75 $\mu$V peak-to-peak. |
| REM | The appearance of low voltage, mixed frequency EEG activity, and episodic rapid eye movements (REMs). |
| MT | A record in which at least 50% of a page (corresponding to 30 seconds) is characterized by an increase in EMG activity. |

[a]cycles per second
[b]Stages 3 and 4 are commonly referred to as Slow Wave Sleep (SWS)

SLEEP ONSET

Behavioural versus Physiological Definitions of Sleep Onset

The correspondence between behavioural and polysomnographic definitions of sleep onset was assessed by comparing mean differences among a number of different polygraphic and and behavioural definitions of sleep onset. Both the behavioural and physiological definitions of sleep onset are presented in Table 2.

TABLE 2

| \multicolumn{2}{l}{Table of Physiological and Behavioural Definitions} |  |
|---|---|
| Definition | Definition of Sleep Onset |
| Physiological |  |
| 1 | First epoch of Stage 1 |
| 2 | First epoch of Stage 1 leading to Stage 2 |
| 3 | First epoch of Stage 2 |
| 4 | First epoch of Stage 2 followed by $>=8$ min. sleep in next 10 min. |
| 5 | First minute of Stage 2 followed by $>=8$ min. sleep in next 9 min. |
| Behavioural |  |
| 6 | First missed response |
| 7 | Two consecutive missed responses |

The criterion of the first missed response to the vibratory stimulus was chosen as an intuitively plausible measure of behaviourally defined sleep onset. Similarly, two consecutive missed responses was chosen to identify the onset of a consolidated sleep period.

The polysomnographic criteria were selected to include a variety of definitions employed in the existing literature. Briefly, these definitions range from the least stringent criterion of the appearance of the first epoch of Stage 1 to a more stringent consolidated criterion requiring the subject to have entered the first minute of Stage 2 sleep that is followed by nine consecutive minutes of sleep (Stage 2, 3, or 4) interrupted by no more than one minute of awake. Lying somewhere in the middle is the most widely used definition of sleep onset, that is the appearance of the first epoch of Stage 2 sleep. These definitions may be roughly grouped into those requiring little or no consolidation (1-3) and those requiring a definite degree of consolidation (4 and 5). Mean sleep onset latencies corresponding to each of the behavioural and physiological definitions are presented in FIG. 3.

Figure 3:
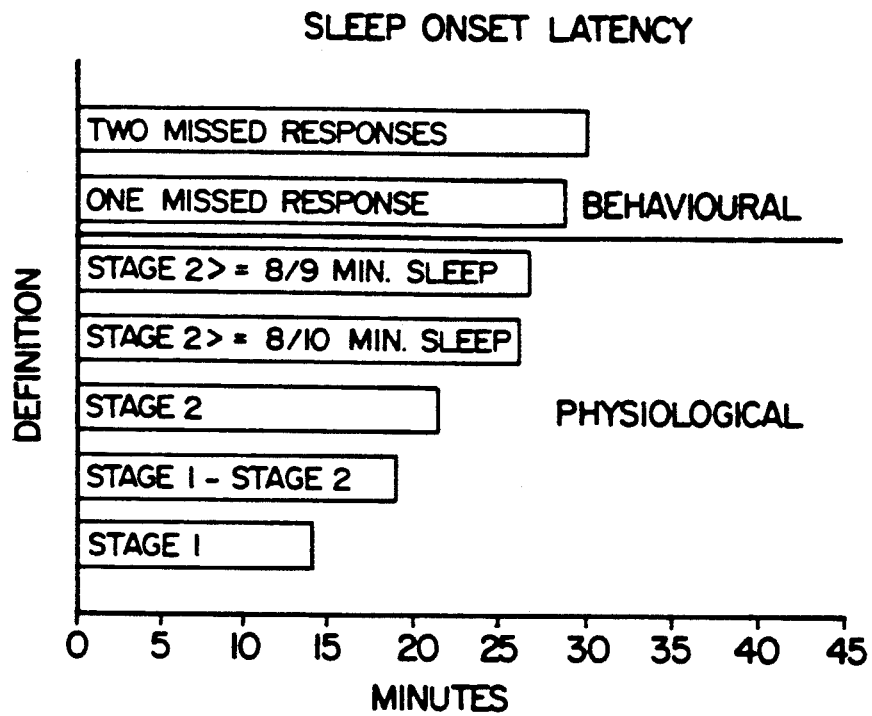
FIG. 3 is a graph illustrating mean sleep onset latencies corresponding to five physiological and two behavioural definitions.

Sleep onset latencies defined by the seven criteria were compared in an analysis of variance in which the definition of sleep onset was extracted as a within subjects factor. A significant effect of definition was found (F(6,66)=8 62; p<0.0013). As can be seen in FIG. 3, this was due mainly to differences between the mean latency defined by the physiological criterion of the first appearance of Stage 1 and the two consolidated sleep onset latency definitions and both of the behavioural definitions of sleep onset latency.

Statistical analysis indicates that the estimates of sleep onset latency provided by the vibratory stimulus device do not differ significantly from those provided by the consolidated physiological definitions of sleep onset.

This suggests that the behavioural criteria define consolidated sleep and can serve as accurate indicators of the onset of polygraphically defined consolidated sleep.

Figure 4:
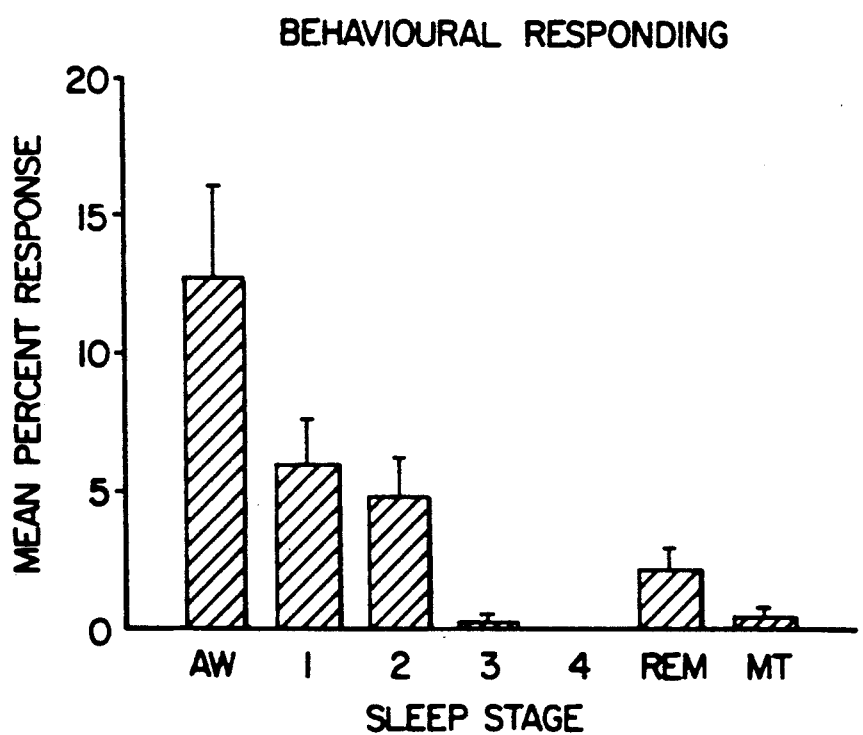
FIG. 4 is a diagram illustrating behavioural response in each stage of sleep.

Relationship of Behavioural Response to Polysomnographically Defined Sleep Stages The mean percent of stimuli responsed to in each sleep stage is illustrated in FIG. 4. As anticipated, the highest level of responding was seen in wakefulness (AW). During sleep a higher level of responding occurred in the 'lighter' stages of sleep (Stage 1 and Stage 2), while little or no responding was seen in the 'deeper' stages (Stages 3 and 4). An intermediate level of responding was found during REM sleep.

Effects of Stimulation on Sleep Architecture

The relationship between the behavioural measure and polysomnographic recording was also examined by correlating the total percent responding of the subjects with various polygraphic measures of sleep. These correlations are presented in Table 3.

Over the whole night, a significant correlation was found between behavioural responding and both total sleep time (r(10)=−0.777; p<0.003) and sleep efficiency (r(10)=−0.819; p<0.001). Thus, those subjects who responded more frequently during the night slept significantly less than subjects who responded less frequently, and their sleep efficiency (calculated by dividing the total sleep time by the total recording time and multiplying by 100) was also significantly reduced.

TABLE 3

Table of Pearson Product Moment Correlation between Mean Percent Responding and Sleep Variables

| Sleep Variable | r | p |
| --- | --- | --- |
| Total Time Recorded (TTR) | 0.298 | n.s. |
| Total Sleep Time (TST) | −0.777 | <0.003 |
| Sleep Efficiency (SE) | −0.819 | <0.002 |
| Sleep Onset Latency (SOL) | 0.568 | n.s. |
| % Awake (PERAW) | 0.838 | <0.001 |
| % Stage 1 (PER1) | 0.727 | <0.01 |
| % Stage 2 (PER2) | −0.747 | <0.006 |
| % Stage 3 (PER3) | −0.371 | n.s. |
| % Stage 4 (PER4) | −0.250 | n.s. |
| % REM (PERREM) | −0.682 | <0.05 |
| % MT (PERMT) | 0.117 | n.s. |
| REM Latency (REML) | 0.614 | <0.05 |
| No of REM Periods (NREMP) | −0.463 | n.s. |
| Shifts to Awake (SHAW) | −0.672 | <0.02 |
| Shifts to Stage 1 (SH1) | 0.501 | n.s. |
| Shifts to MT (SHMT) | 0.146 | n.s. |
| % SWS (PERSWS) | −0.593 | <0.05 |
| Shifts to Aw + 1 + MT (SHAW1MT) | 0.664 | <0.02 |

Mean percent responding over the night was also correlated with the different stages of sleep. It was found that, in general, wakefulness (r(10)=0.838; p<0.0007) and Stage I (r(10)=0.727; p<0.008) correlated positively with behavioural responding, while 'deeper' stages of sleep (Stages 3 and 4) correlated negatively. This suggests that the more frequently subjects responded, the more time they spent awake and in Stage 1, and the less time they tended to spend in SWS (r(10)=0.592; p<0.05). The amount of time spent in Stage 2 sleep was also found to be significantly correlated with percent responding (r(10)=−0.746; p<0.005). Subjects who responded with greater frequency to the stimulus spent significantly less time in Stage 2 sleep. A significant correlation was also found between mean percent responding and shifts to awake (r(10)=0.672; p<0.02), indicating that more frequent responding was associated with more shifts to awake.

A significant negative correlation was also found between mean percent responding and percentage of REM sleep (r(10)=−0.682; p<0.01). Subjects who responded more often to the vibratory stimulus had significantly less REM sleep than those subjects who responded less frequently. Finally, percent responding was found to be significantly correlated with REM latency (r(10)=0.614; p<0.03), which is defined as the interval of time between sleep onset and the beginning of the first REM period. Thus, REM latency was significantly longer for those subjects who responded more frequently to the vibratory stimulus.

It is evident that a substantial relationship exists between sleep assessed behaviourally and polygraphically.

Sleep Disturbance Produced by the Vibratory Stimulus

Although the parameters of the stimulus presentation were chosen so as to minimize the possibility of disturbing the subjects' sleep, the extent to which sleep might differ from that usually experienced was assessed in two ways: by examining the subjects' subjective appraisal of their experience and their polysomnographically defined sleep. It is generally known that sleeping in a new environment produces a 'first night effect', that is sleep may be more disturbed than that which occurs in an environment which is familiar.

In the morning subjects were asked a number of questions to obtain information on their own experience during the study. On average subjects estimated that they experienced 8 vibrations a night while, in fact, they received an average of about 50 per night. Half the subjects indicated that their sleep was the same as a 'normal' night's sleep at home and half indicated that it was worse, a finding that is typically obtained after the first night in a sleep laboratory.

A number of polygraphic parameters were compared with a sample of approximately the same age who were also spending their first night in the laboratory but who were allowed to sleep undisturbed. The results indicated differences in Stage 1, Stage 2, Slow Wave Sleep (Stages 3 and 4) and Movement Time. Overall the degree of disturbance averaged slightly over 4 percent of the total night's sleep.

Overall, by both subjective and polygraphic criteria, the sleep of the subjects was disturbed to some degree by the vibratory units. However, the amount of disturbance appears to be quite small and insufficient to invalidate the general conclusions regarding the efficacy of this device.

We claim:

1. An apparatus for monitoring sleep behaviour in a human subject, comprising:
    a housing;

vibratory means and subject response means contained within said housing;

timing means to activate said vibratory means at selected time intervals for selected periods of time;

means to record and store each activation event of said vibratory means, and subject positive and negative response thereto; and means to retrieve and analyze said records.

2. An apparatus as claimed in claim 1 wherein said housing is a handheld housing and includes means to releasably secure said housing to a subject's hand.

3. An apparatus as claimed in claim 2 wherein said timing means and said means to record are contained within said housing.

4. An apparatus as claimed in claim 3 including a power source, within said housing, to activate said vibratory means, said timing means and said record means.

5. An apparatus as claimed in claim 2 wherein said means to releasably secure said housing comprises strap means secured at each end in spaced relationship to each other to said housing so as to provide a loop through which a hand may be inserted.

6. An apparatus as claimed in claim 5 wherein said subject response means comprises a microswitch.

7. An apparatus as claimed in claim 5 wherein said vibratory means comprises an electro tactile vibrator operable at a frequency of between 160 and 200 Hz with a 20–40 Hz band width.

8. A method for assessing sleep behaviour in a human subject, comprising:

(a) subjecting the subject to a vibratory stimulus for a selected period of time at selected spaced intervals of time, (b) recording the time of each said stimulus and the subject's response or lack thereof to each said stimulus, (c) recovering stored information; and assessing the subject by comparison of said recovered stored information with known standards of sleep behaviour.

9. A method as claimed in claim 8 wherein said vibratory stimulus is administered at intervals of between 5 and 10 minutes over a period of at least 5 hours.

10. A method as claimed in claim 9 wherein each said stimulus is administered for about 0.5 seconds.

11. A method as claimed in claim 10 wherein said stimulus has a frequency of between 160 and 200 Hz with a band width of about 20–40 Hz.

12. A method as claimed in claim 11 wherein said vibratory stimulus is provided by a hand held vibratory means which also contains a timer means and means to record and store information relating to each said stimulus and each response thereto.

* * * * *